United States Patent [19]

Kober et al.

[11] Patent Number: 5,093,046
[45] Date of Patent: Mar. 3, 1992

[54] PREPARATION OF ETHEREAL SOLUTIONS OF ARYLMETHYL-MAGNESIUM HALIDES

[75] Inventors: Reiner Kober; Rainer Seele, both of Fussgoenheim; Thomas Zierke, Boehl-Iggelheim; Heinz Isak, Mutterstadt; Stefan Karbach, Neustadt; Guenter Wegner, Speyer, all of Fed. Rep. of Germany

[73] Assignee: BASF Aktiengesellschaft, Ludwigshafen, Fed. Rep. of Germany

[21] Appl. No.: 575,803

[22] Filed: Aug. 31, 1990

[30] Foreign Application Priority Data

Aug. 31, 1989 [DE] Fed. Rep. of Germany ....... 3928812

[51] Int. Cl.$^5$ ............................................... C07F 3/02
[52] U.S. Cl. ............................................... 260/665 G
[58] Field of Search ........................................ 260/668

[56] References Cited

U.S. PATENT DOCUMENTS 2,890,176 6/1959 Ramsden et al. ................... 260/665

FOREIGN PATENT DOCUMENTS 1332718 10/1973 United Kingdom .

OTHER PUBLICATIONS

Methoden der Organischen Chemie, vol. XIII/2a, 1973, p. 79, E. Muller et al., "Grignard-Verbindungen Aus Organischen Halogeniden".

Journal of the American Chemical Society, 95:18, Sep. 5, 1973, pp. 5919–5924, M. Y. Darensbourg et al., "Electronic and Steric Control of Reactions of Benzylmagnesium Chloride With Substituted Metal Carbonyls".

Bulletin of the Chemical Society of Japan, vol. 50, (9), pp. 2379–2384, 1977, M. Okubo, "Ketyl Radicals Formed in Grignard Reaction. 1V$^1$) Sterically Hindered Ketyl Radicals in Nuclear Replacement and Conjugate Addition".

Primary Examiner—Arthur C. Prescott
Attorney, Agent, or Firm—Oblon, Spivak, McClelland, Maier & Neustadt

[57] ABSTRACT

Ethereal solutions of arylmethylmagnesium halides $$\text{Ar—CH}_2\text{—Mg—Hal} \qquad \text{I}$$

(where Ar is unsubstituted or substituted aryl and Hal is Cl or Br) are prepared by the Grignard method from an arylmethyl halide II $$\text{Ar—CH}_2\text{—Hal} \qquad \text{II}$$

and magnesium in an ether III $$\text{tert-butyl—O—R} \qquad \text{III}$$

(where R is $C_1$–$C_3$-alkyl) as solvent.

4 Claims, No Drawings

PREPARATION OF ETHEREAL SOLUTIONS OF ARYLMETHYL-MAGNESIUM HALIDES

The present invention relates to an improved process for the preparation of ethereal solutions of arylmethyl-magnesium halides of the general formula I $$Ar-CH_2-Mg-Hal \qquad I$$

where Ar is unsubstituted or substituted aryl and Hal is chlorine or bromine, by reacting an arylmethyl halide of the general formula II $$Ar-CH_2-Hal \qquad II$$

with magnesium in an ether as a solvent.

This process for the preparation of the compounds I, which are usually referred to as arylmethyl Grignard compounds, is generally known in various forms for many special cases (for example Houben-Weyl, Vol. XIII/2a, page 79, Thieme Verlag, Stuttgart, 1973). The ethereal solvent mainly used is diethyl ether, although it requires expensive safety measures in terms of process engineering, owing to its high volatility, its low flashpoint and the tendency to form highly explosive peroxides.

On the other hand, other ethers, such as tetrahydrofuran (J. Am. Chem. Soc. 95 (1973), 5919 and Bull. Chem. Soc. Jap. 50 (1977), 2379), and glycol dimethyl ether (German Laid-Open Application DOS 2,149,087), have proven suitable for conversion of arylmethyl halides into Grignard compounds only in exceptional cases because, particularly in this case, the Grignard reaction is accompanied by highly undesirable dimerization $$Ar-CH_2-Mg-Hal + Hal-CH_2-Ar \rightarrow Ar-CH_2-CH_2-Ar + MgHal_2.$$

In spite of the stated disadvantages, chiefly diethyl ether is used as the reaction medium because the dimerization is least troublesome in this case.

It is an object of the present invention to provide an improved process for the preparation of the compounds I, in which undesirable dimerization is suppressed and which gives high yields of the compounds I and is more advantageous with regard to safety and hence economically as compared with the procedure using diethyl ether as a solvent.

We have found that this object is achieved by an improved process for the preparation of ethereal solutions of arylmethylmagnesium halides of the general formula I $$Ar-CH_2-Mg-Hal \qquad I$$

where Ar is unsubstituted or substituted aryl and Hal is chlorine or bromine, by reacting an arylmethyl halide of the general formula II $$Ar-CH_2-Hal \qquad II$$

with magnesium in an ether as a solvent, wherein the solvent used is an ether of the general formula III $$\text{tert-butyl-O-R} \qquad III$$

where R is $C_1-C_3$-alkyl.

Observations to date have shown that the success of the novel process is not dependent on the type of radical Ar, unless this radical carries substituents which are reactive under the reaction conditions.

Suitable starting compounds II, among which the arylmethyl chloride compounds are generally preferred, are the parent compounds of this class, including in particular the benzyl halides and in addition the halomethylnaphthalenes and the halomethylanthracenes, which in turn may preferably carry not more than three substituents which are inert under the conditions of the Grignard reaction.

Examples of substituents are
halogen, such as fluorine, chlorine or bromine,
$C_1-C_8$-alkyl, including preferably methyl, ethyl, isopropyl and tert-butyl,
multi-membered methylene bridges which are bonded to the aryl ring in the ortho position, including preferably the tetramethylene unit,
$C_1-C_6$-haloalkyl, having fluorine and/or chlorine as halogen atoms, including preferably trifluoromethyl,
$C_1-C_6$-alkoxy, including preferably methoxy,
$C_1-C_6$-haloalkoxy having fluorine and/or chlorine as halogen atoms, including preferably tetrafluoroethoxy,
$C_2-C_6$-alkenyl, including preferably isopropenyl,
$C_3-C_6$-cycloalkyl, including preferably cyclopentyl and cyclohexyl,
trimethylsilyl and
the phenyl and phenoxy group, which in turn may carry the abovementioned substituents.

Examples of compounds II, which are particularly important because of their use for organic syntheses in the areas of crop protection agents, drugs and dyes, are:
benzyl chloride
4-chlorobenzyl chloride
4-fluorobenzyl chloride
3-bromobenzyl chloride
4-methylbenzyl chloride
4-methoxybenzyl chloride
2,5-dimethylbenzyl chloride
2-chloromethylnaphthalene and
2-chloromethyl-5,6,7,8-tetrahydronaphthalene.

The amount of solvents to be used according to the invention, among which tert-butyl methyl ether is preferred, is in general from 3 to 30, preferably from 8 to 15, times the amount of starting compound II.

The amount of magnesium, which is preferably used in the form of turnings, is not less than 1 mol per mol of II for complete conversion of II.

However, for increasing the yield and also for further suppressing dimerization, a molar ratio of Mg:II of from 2.5:1 to 20:1, in particular from 5:1 to 12:1, is advisable.

The reaction temperatures are preferably from $-10°$ to $100°$ C., in particular from $0°$ to $60°$ C., the reaction generally being carried out under atmospheric pressure and under an inert gas atmosphere (e.g. under nitrogen).

It is advantageous to use a concentrated solution at the beginning of the reaction and then gradually to add the remaining amount of the solvent.

Otherwise, the Grignard reaction is carried out in the conventional manner, so that further information is unnecessary.

The Grignard solutions of I which are obtainable according to the invention are stable and are used in this form directly for further reactions. For example, 2-chlorobenzylmagnesium chloride and chloromethyl 4-fluorophenyl ketone give 1-chloro-2-(4-fluorophenyl)-3-(2-chlorophenyl)-propan-2-ol, from which in turn the fungicide cis-1-(2-chlorophenyl)-2-(4-fluorophenyl)-3-(1,2,4-triazol-1-yl)-prop-1-ene (German Laid-Open Application DOS 2,652,313) is prepared.

EXAMPLES

A solution of 16 g (0.1 mol) of 2-chlorobenzyl chloride and 30 g of tert-butyl methyl ether was added to 2.9 g (0.12 mol) of magnesium in 18 g of tert-butyl methyl ether at 25° C. under a nitrogen atmosphere in the course of 1.5 hours, the reaction being initiated with a little 1,2-dibromoethane. To complete the reaction, stirring was carried out for 3 hours at 35° C.

Water was then added to the reaction mixture, the Grignard compound being hydrolyzed to 2-chlorotoluene and a little 2-chlorobenzyl alcohol. The organic phase was then analyzed by HPCL to determine the yields of 2-chlorotoluene and 2-chlorobenzyl alcohol, which together correspond to the yield of the Grignard compound, to determine the unconverted 2-chlorobenzyl chloride and to determine the yield of the undesirable compound 1,2-di-(2-chlorophenyl)-ethane.

The experiment was repeated with 14.4 g (0.6 mol) of magnesium, and 14.5 g (0.1 mol) of 4-fluorobenzyl chloride were subjected to the Grignard reaction in the same manner, likewise with 14.4 g (0.6 mol) of magnesium. For comparison, these reactions were also carried out in other ethers as solvents.

The details of these experiments and the results are shown in the Table below.

naphtalenes, and anthracenes and Hal is chlorine or bromine, by reacting an arylmethyl halide of the formula II $$Ar-CH_2-Hal \qquad \qquad II$$

with magnesium in an ether as a solvent at a temperature from $-10°$ to $+100°$ C., wherein the solvent used is an ether of the formula III $$\text{tert-butyl-O-R} \qquad \qquad III$$

where R is $C_1-C_3$-alkyl.

2. A process as claimed in claim 1, wherein the amount of magnesium used is from 2.5 to 20 mol per mol of the starting compound II.

3. A process as claimed in claim 1, wherein starting compound II used is the chloride (Hal=Cl).

4. A process as claimed in claim 1, which is used for the conversion of benzyl halides whose phenyl groups may carry not more than three of the following substituents:

fluorine, chlorine, bromine,
$C_1-C_8$-alkyl,
$C_1-C_6$-haloalkyl having fluorine and/or chlorine as halogen atoms,
$C_1-C_6$-alkoxy,
$C_1-C_6$-haloalkoxy having fluorine and/or chlorine as

| Experiment No. | Starting compound II | Ether | Ratio mol Mg/mol II | Conversion of II [%]* | Yield [%]* of Grignard compound | Dimer formation** [%]* |
|---|---|---|---|---|---|---|
| According to the invention | | | | | | |
| 1 | 2-Cl-Ph-CH$_2$Cl | tert-butyl-O-Me | 1.2 | >95 | 75-80 | 10-15 |
| 2 | 2-Cl-Ph-CH$_2$Cl | tert-butyl-O-Me | 6.0 | 95 | 85-90 | 0-5 |
| 3 | 4-F-Ph-CH$_2$Cl | tert-butyl-O-Me | 6.0 | >98 | 64.7 | 25.6 |
| For comparison | | | | | | |
| 4 | 4-F-Ph-CH$_2$Cl | tetrahydrofuran | 1.2 | 99.8 | 49.9 | 47 |
| 5 | 2-Cl-Ph-CH$_2$Cl | tetrahydrofuran | 1.2 | >73 | 0-5 | >68 |
| 6 | 2-Cl-Ph-CH$_2$Cl | glycol dimethyl ether | 1.2 | >95 | 0-5 | >90 |
| 7 | 2-Cl-Ph-CH$_2$Cl | n-dibutyl ether | 1.2 | 68 | 0-5 | 44 |
| 8 | 2-Cl-Ph-CH$_2$Cl | diisopropyl ether | 1.2 | 61 | 0-5 | 35 |
| 9 | 2-Cl-Ph-CH$_2$Cl | diethyl ether | 1.2 | 98.7 | 85-90 | <5 |
| 10 | 4-F-Ph-CH$_2$Cl | tetrahydrofuran | 6.0 | 99.8 | 56 | 40 |
| 11 | 2-Cl-Ph-CH$_2$Cl | tetrahydrofuran | 6.0 | >95 | 0-5 | >90 |

*Relative percentages by area
**1,2-Di-(chlorophenyl)-ethane or 1,2-di-(4-fluorophenyl)-ethane

We claim:
1. A process for the preparation of an ethereal solution of an arylmethylmagnesium halide of the formula I

$$Ar-CH_2-Mg-Hal \qquad \qquad I$$

where Ar is unsubstituted or substituted aryl wherein the aryl is selected from the group consisting of phenyl, halogen atoms,
$C_2-C_6$-alkenyl,
$C_3-C_6$-cycloalkyl,
trimethylsilyl and
the phenyl and phenoxy group, which in turn may carry the abovementioned substituents.

* * * * *